United States Patent [19]

Umezawa et al.

[11] Patent Number: 4,686,308
[45] Date of Patent: Aug. 11, 1987

[54] NOVEL PHYSIOLOGICALLY ACTIVE SUBSTANCE MH435

[75] Inventors: Hamao Umezawa; Tomio Takeuchi; Masa Hamada; Hiroshi Naganawa, all of Tokyo; Tsutomu Sawa, Ayase; Masaya Imoto, Urawa; Hironobu Iinuma, Wako; Takeshi Uchida, Takasaki; Kunio Isshiki, Fujisawa, all of Japan

[73] Assignee: Microbial Chemistry Research Foundation, Tokyo, Japan

[21] Appl. No.: 879,069

[22] Filed: Jun. 26, 1986

[30] Foreign Application Priority Data

Jul. 4, 1985 [JP] Japan .................................. 60-147039

[51] Int. Cl.4 ........................................ C07C 103/34
[52] U.S. Cl. .................... 564/219; 435/129
[58] Field of Search .......................... 564/219

[56] References Cited

U.S. PATENT DOCUMENTS

| | | | |
|---|---|---|---|
| 2,588,968 | 3/1951 | Dickey et al. | 564/219 X |
| 3,689,557 | 9/1972 | McCaully et al. | 569/219 X |
| 3,714,229 | 1/1973 | Saari et al. | 564/219 X |
| 3,832,365 | 8/1974 | Wehrci | 564/219 X |
| 3,944,675 | 3/1976 | Symchowicz et al. | 564/219 X |
| 4,014,937 | 3/1977 | Richardson | 564/219 X |
| 4,053,509 | 10/1977 | Faro et al. | 564/219 X |
| 4,588,836 | 5/1986 | Matsumoto et al. | 564/219 X |

*Primary Examiner*—Paul F. Shaver
*Attorney, Agent, or Firm*—Ladas & Parry

[57] ABSTRACT

Disclosed is a novel physiologically active substance, MH435, represented by the formula:

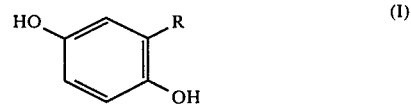

wherein R represents either of the following groups A and B

A: —CH=CH—NHCHO
B: —CH$_2$—CH$_2$—NHCHO.

The substance MH435 has an inhibitory activity against tyrosine specific protein kinase, and the 50% inhibitory concentrations of the substances MH435-A and MH435-B are respectively 0.55 μg/ml and 6.0 μg/ml.

3 Claims, No Drawings

NOVEL PHYSIOLOGICALLY ACTIVE SUBSTANCE MH435

BACKGROUND OF THE INVENTION

1. Field of the Art

This invention relates to a novel substance, more particularly a novel physiologically active substance, MH435, having antitumor activity and antimicrobial activity.

A considerable number of substances have already been put to practical use as antitumor agents and antimicrobial agents, but they are not always satisfactory in pharmaceutical activity and/or the matter of side effect. Thus, there still remains a need for improved novel antitumor agents and antimicrobial agents.

2. Prior Art

Bishop, J. M. has reported that a product of certain cancer genes has a tyrosine specific protein kinase activity [Ann. Rev. Biochem., 52, 301-354 (1983)]. Cohen et al. have described in their report that the tyrosine specific protein kinase has a role as a signal substance in the processes of cell proliferation owing to many cell growth factors [J. Biol. Chem., 257, 1523-1531 (1982)].

SUMMARY OF THE INVENTION

With these results in view, we have screened a variety of substances in natural occurrence for the purpose of finding inhibitors of the tyrosine specific protein kinase activity. As a result of the screening, we have found that these inhibitors have antitumor activity and antimicrobial activity.

The novel physiologically active substance according to this invention is represented by the formula:

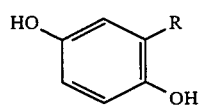
(I)

wherein R represents either of the following groups A and B
A: —CH=CH—NHCHO
B: —CH$_2$—CH$_2$—NHCHO.

DETAILED DESCRIPTION OF THE INVENTION

Novel Physiologically Active Substance MH435

1. Chemical Structure

The substance MH435 has a chemical structure represented by the formula (I) set forth above.

Depending on the type of the substituent R, the substance MH435 includes two species, viz. MH435-A and MH435-B.

2. Physicochemical Properties

The physical properties of the substance MH435 are set forth in the following Table 1.

TABLE 1

|  | MH435-A |  |  | MH435-B |  |  |
|---|---|---|---|---|---|---|
| Melting point | 78–82° C. |  |  |  |  |  |
| Molecular weight | 179 |  |  | 181 |  |  |
| Molecular formula | C$_9$H$_9$O$_3$N |  |  | C$_9$H$_{11}$O$_3$N |  |  |
| Elementary analysis | C | H | O | C | H | O |
| Found: | 60.3 | 5.1 | 26.8 | 59.7 | 6.1 | 26.5 |
| Calculated: | 60.3 | 5.1 | 26.8 | 59.7 | 6.1 | 26.5 |
| UV and visible absorption spectrum ($\lambda_{max}$,nm) | 330,275,208 |  |  | 295,235 |  |  |
| IR absorption spectrum (K Br tab.; cm$^{-1}$) | 1650, 1540, 1510, 1400, 1320, 1260, 1200, 960, 820, 780 |  |  | 1650, 1510, 1460, 1380, 1200, 820 |  |  |
| NMR spectrum ($^1$H-NMR;δ) | 6.45(d), 6.50(dd), 6.68(d), 6.72(d), 6.80(d), 7.70(s), 8.00(s), 8.15(s), 9.28(s) |  |  | 2.77(t), 3.50(t), 6.58(dd), 6.68(d), 6.70(s), 7.78(s), 8.00(s), 8.25(s), 8.40(s) |  |  |
| Rf values*$^1$ | 0.36(Chloroform:Methanol = 10:2) 0.24(Toluene:Acetone = 1:1) |  |  | 0.36(Chloroform:Methanol = 10:2) 0.12(Toluene:Acetone = 1:1) |  |  |
| Appearance | Pale yellow |  |  | Pale yellow |  |  |

*$^1$measured with "KIESELGEL 60" manufactured by Merck & Co.

Preparation of MH435

1. Summary

MH435 is currently prepared only by the cultivation of a microorganism (for MH435-A) and by the synthetic chemical modification of the cultivation product of MH435-A (for MH435-B). It may also be prepared by other processes, for example, total synthesis by a chemical method.

As the microbial strain used for the process by the cultivation of a microorganism, strains of the genus Streptomyces having MH435-A-producing capability are used. Specifically, we have shown that the MH435-hF3 strain we have isolated, which will be described in more detail hereinbelow, produces MH435-A. It is possible to isolate other strains which are suitable for producing the substance from natural sources by the conventional method of isolating antibiotic-producing microorganisms. It is also possible to increase the MH435-A-producing capacity by subjecting the MH435-A-producing microorganisms including the MH435-hF3 strain to mutation treatment such as irradiation by a high energy ray such as UV. Furthermore, it may also be possible to derive the MH435-A-producing microorganisms by subjecting the gene DNA which carries genetic informations with respect to the production of MH435-A to recombinant DNA techniques such as transformation and cell fusion.

2. Strain MH435-hF3

The strain MH435-hF3 that we have found as a strain of the genus Streptomyces having the MH435-A-producing capacity will now be described.

(A) Source and accession number

The strain MH435-hF3 is an actinomycete which was isolated from the soil in the grounds of the Institute of Microbiological Chemistry, Japan, in November, 1984. It was deposited with the Fermentation Research Institute, Agency of Industrial Science and Technology, Japan, on May 21, 1985 and was assigned an accession number: FERM P-8246. This strain now bears the accession number FERM BP-1082 under the terms of the Budapest Treaty on the International Recognition of the Deposit of Microorganisms for the Purposes of Patent Procedure. This depository fully complies with the rules of the Budapest Treaty. Specifically, it fully complies with Rule 11.3 of the Budapest Treaty whereby the organism is available to the public on patent grant and with Rule 9 of the Budapest Treaty which requires the maintenance of the organism for a period of at least 30 years after the date of deposit.

(B) Microbiological properties of the strain MH435-hF3

(1) Morphology

The strain MH435-hF3 under microscopic observation extends aerial mycelia having spiral hyphae from branched substrate mycelia with no verticil branch. Chains of 10 or more spores in matured spore chains, wherein the size of the spores is in the range of about $0.6-0.8 \times 1.0-1.2$ μ, are observed. The spores have projections in the form of relatively long prickles.

(2) Cultural Characteristics

Information will be given below, in which the description of color in parentheses is carried out in accordance with the Color Harmony Manual of the Container Corporation of America.

(i) Sucrose-nitrate agar (incubated at 27° C.)

On colorless growth, yellowish brown (2 ni, Mustard Brown) to brownish gray (2 li Covert Brown) aerial mycelium develops. No soluble pigment.

(ii) Glucose-asparagine agar (incubated at 27° C.)

On pale yellow growth, light olive gray to olive gray (1½ ig, Olive Gray—1½ li Lt Olive Drab—2 li Covert Brown) aerial mycelium develops. No soluble pigment.

(iii) Glycerol-asparagine agar (ISP medium No. 5, incubated at 27° C.)

On pale yellowish brown (2 le, Mustard—3 pg, Golden Brown) growth, light gray to light olive gray (1 fe, Griege—1½ ge, Lt Olive Gray) aerial mycelium develops. The soluble pigment is tinged with yellowish brown.

(iv) Starch-inorganic salt agar (ISP medium No. 4, incubated at 27° C.)

On colorless growth, grayish olive (2 ni, Mustard Brown) aerial mycelium develops. The soluble pigment is slightly tinged with brown.

(v) Tyrosine agar (ISP medium No. 7, incubated at 27° C.)

On pale yellowish brown (2 gc, Bamboo—2 le, Mustard) to yellowish brown (3 ng, Yellow Maple) growth, brownish white to light olive gray (1 ge, Citron Gray—1½ ge, Lt Olive Gray—1½ ig, Olive Gray) aerial mycelium develops. The soluble pigment is tinged with yellowish brown.

(vi) Nutrient agar (incubated at 27° C.)

Growth is tinged with pale yellowish brown (2 gc, Bamboo) with no aerial mycelium. No soluble pigment.

(vii) Yeast-malt agar (ISP medium No. 2, incubated at 27° C.)

On pale yellowish brown (3 le, Cinnamon—3 pg, Golden Brown) growth, light olive gray (1½ lg, Golden Olive) to olive gray (1½ ni, Olive) aerial mycelium develops. The soluble pigment is slightly tinged with brown.

(viii) Oatmeal agar (ISP medium No. 3, incubated at 27° C.)

On colorless to pale yellow growth, aerial mycelium develops. The soluble pigment is slightly tinged with brown.

(ix) Glycerol-nitrate agar (incubated at 27° C.)

Growth is tinged with pale yellow (2 gc, Bamboo). No aerial mycelium develops or white aerial mycelium develops scantily. The soluble pigment is slightly tinged with brown.

(x) Starch agar (incubated at 27° C.)

On colorless growth, yellowish brown aerial mycelium develops. No soluble pigment.

(xi) Calcium malate agar (incubated at 27° C.)

Growth is tinged with pale yellowish brown (2 ge, Bamboo). No aerial mycelium develops or light olive gray aerial mycelium develops scantily. No soluble pigment.

(xii) Cellulose (incubated at 27° C.)

Growth is colorless, and light olive gray aerial mycelium develops scantily. No soluble pigment.

(xiii) Gelatin stab culture medium

In simple gelatin medium (cultured at 20° C.), growth is colorless or tinged with pale yellow. No aerial mycelium develops, nor is produced soluble pigment. In glucose-peptone-gelatin medium (incubated at 27° C.), growth is tinged with pale yellow. No aerial mycelium develops, nor is produced soluble pigment.

(xiv) Skimmed milk (incubated at 27° C. and 37° C.)

On incubation at 27° C., white aerial mycelium slightly develops on pale yellow growth, and no soluble pigment is produced. On incubation at 37° C., growth is rather poor and tinged with pale yellow. No aerial mycelium develops, nor is produced soluble pigment.

(3) Physiological Properties (i) Growth temperature range

When tests were carried out at temperatures of 20° C., 24° C., 27° C., 30° C., 37° C. and 50° C. using the starch-inorganic salt agar medium (ISP medium No. 4), growth was observed at all these temperatures, except at 50° C., among which the optimum temperature is presumably around 30° C.

(ii) Liquefaction of gelatin (15% simple gelatin: incubated at 20° C.; and glucose-peptone-gelatin: incubated at 27° C.)

Liquefaction begins after ca. 4 days of incubation on the simple gelatin medium, while it begins after ca. 3 days of incubation on the glucose-peptone-gelatin medium. The liquefactive strength is moderate to strong.

(iii) Hydrolysis of starch (Starch-inorganic salt agar medium and starch agar medium)

Negative on either medium.

(iv) Coagulation and peptonization of skimmed milk (skimmed milk, incubated at 27° C. and 37° C.)

Peptonization begins without coagulation after ca. 10 days of incubation at 27° C., and the strength is moderate to strong. On the other hand, peptonization begins after ca. 14 days of incubation at 37° C. in which growth is rather poor, and the strength is moderate to weak.

(v) Production of melanoid pigment (tryptone-yeast extract broth, ISP medium No. 1: peptone-yeast extract-iron agar, ISP medium No. 6: tyrosine agar, ISP medium No. 7, each incubated at 27° C.)

Negative on any of the media.

(vi) Utilization of carbon sources (Pridham-Gottlieb agar medium, ISP medium No. 9; incubated at 27° C.)

Glucose, raffinose and D-mannitol are utilizable for growth and L-arabinose is probably utilizable, but sucrose and rhamnose are not utilizable. It is questionable whether D-xylose, D-fructose and inositol are utilizable or not.

(vii) Dissolution of calcium malate (calcium malate agar, incubated at 27° C.)

Calcium malate is dissolved around the periphery of growth after ca. 7 days of cultivation. The dissolving action is moderate to strong.

(ix) Nitrate reduction (0.1% potassium nitrate-containing peptone water, ISP medium No. 8; incubated at 27° C.)

Negative or positive depending upon the case in repeated tests.

To sum up the above described properties, no sporangium is observed in the strain MH435-hF3. The aerial mycelium is spiral in configuration with no verticil branch. The surface of the spore is covered with prickles. On various culture media, the growths are colorless to pale yellow or pale yellowish brown, and the aerial mycelia are light olive gray to olive gray or yellowish brown. The soluble pigment is slightly tinged with brown to yellowish brown. Production of a melanoid pigment is negative, and hydrolysis of starch is not observed. The proteolytic ability is moderate to strong.

The 2,6-diaminopimelic acid contained in the whole bacterial cell of the strain is of the LL-type. In view of this feature together with the aforementioned features, it is apparent that the strain MH435-hF3 belongs to the genus Streptomyces.

On searching for known strains similar to the strain MH435-hF3 based on these features, this strain has been found to be close to the following three strains:

*Streptomyces viridosporus* [lit.: International Journal of Systematic Bacteriology, 22, 371 (1972) (lit. 1), and UKP No. 712,547 (lit. 2)],

*Streptomyces viridodiastaticus* [lit.: ibid., 19, 500 (1969); ibid., 30, 405 (1980)] and

*Streptomyces mitakaensis* [lit.: The Journal of Antibiotics, Series A, 11, 14 (1958)].

*Streptomyces viridodiastaticus* (IMC S-0350 [ISP5249]) and *Streptomyces mitakaensis* (IMCS-0508 [NIHJ77]) are very close to each other, but these two strains were clearly distinguished from the strain MH435-hF3 by comparison tests with respect to their microscopic observations, particularly aerial mycelium formation and spiral formation at the head thereof, colors of aerial mycelia, peptonization of milk, etc. The results of comparison tests of the strain MH435-hF3 with the remaining *Streptomyces viridosporus* are shown in Table 2 below.

TABLE 2

|  | MH435-hF3 | Streptomyces viridosporus, IMCS-0696 (ISP5243) |
| --- | --- | --- |
| Formation of verticil branch | − | − |
| Spiral formation | + | + |
| Surface of Spore | prickly | prickly, prickly to hairy*2 |
| Color of aerial mycelium | light olive gray to olive gray | light olive gray to olive gray |
| Color of growth | colorless to pale yellow, pale yellowish brown | pale yellow to pale yellowish brown |
| Soluble pigment | − to pale brown | − |
| Formation of melanoid pigment |  |  |
| ISP medium No. 1 | − | − |
| ISP medium No. 6 | − | − |

TABLE 2-continued

|  | MH435-hF3 | Streptomyces viridosporus, IMCS-0696 (ISP5243) |
| --- | --- | --- |
| ISP medium No. 7 | − | − |
| Hydrolysis of starch | − | + |
| Coagulation of milk | − | − |
| Peptonization of milk | + | + (+*3) |
| Liquefaction of gelatin |  | (+*3) |
| Simple gelatin | + | + |
| Glucose-peptone-gelatin | + | + weak |
| Nitrate reduction | − or + | − |
| Utilization of carbon sources*1 |  |  |
| Glucose | + | + |
| L-Arabinose | (+) | + |
| D-Xylose | ± | + |
| D-Fructose | ± | + |
| Sucrose | − | − |
| Inositol | ± | + |
| Rhamnose | − | + |
| Raffinose | + | − |
| D-Mannitol | + | + |

*1 +: positive utilization; (+): probable utilization; ±: questionable utilization; −: no utilization.
*2 the aforementioned lit. 1.
*3 the aforementioned lit. 2.

As is apparent from Table 2, the strain MH435-hF3 and *Streptomyces viridosporus* are different in hydrolysis of starch and utilization of carbon sources (raffinose and rhamnose). Furthermore, according to the description in the literature, there is some difference in the surface structures of the spores. However, when the surface structures of the two strains are observed, the projections on the spore surface of *Streptomyces viridosporus* are thicker at their bases and may be properly defined as being like elongated prickles rather than hair. The strain MH435-hF3 has also projections in the form of elongated prickles. Therefore, these surface structures can hardly be considered distinct from each other. Moreover, the other properties of the two strains are very similar to each other, and coincide with each other, particularly in respect of the microscopic observation that the aerial mycelia are light olive gray to olive gray and of the peptonization of skimmed milk without coagulation.

From these results, the strain MH435-hF3 is of a species closest to *Streptomyces viridosporus*, but they can hardly be regarded as falling under the same species. Therefore, the strain MH435-hF3 is designated as Streptomyces sp. MH435-hF3.

3. Cultivation/Production of MH435-A

The substance MH435-A can be produced by incubating an MH435-A-producing Streptomyces strain aerobically in a suitable medium and separating the objective substance from the culture.

The culture medium may be one containing any nutrient sources which can be utilized by MH435-A-producing microorganisms. For example, glycerol, glucose, sucrose, maltose, dextrin, starch, fats and oils are useful as carbon sources. As nitrogen sources, organic materials such as soybean meal, cotton seed meal, meat extract, peptone, dry yeast, yeast extract and corn steep liquor, and inorganic materials such as ammonium salts or nitrates, for example, ammonium nitrate, sodium nitrate and ammonium chloride can be used. If necessary, inorganic salts such as sodium chloride, potassium chloride, phosphates, heavy metal salts can also be added. For the purpose of suppressing foaming during fermentation, it is also possible to add an appropriate anti-foaming agent such as silicone or soybean oil in accordance with customary methods.

The most suitable cultivation method is submerged aerobic liquid culture which is employed usually for producing antibiotics. The suitable cultivation temperature is in the range of 20°-35° C., preferably 25°-30° C. When this method is used, the production output of the substance MH435-A reaches a maximum after 2 to 4 days of either shake culture or aerated stirring culture.

Thus, there can be obtained a cultured broth in which the substance MH435-A is accumulated. In the cultured broth, the substance MH435-A is present partly within the mycelium, but most part thereof is present in the supernatant of the cultured broth.

In order to recover the substance MH435-A from the cultured broth, it is possible to employ any methods suitable for the recovery. One of the methods is based on extraction. For example, the substance MH435-A in the supernatant can be recovered by extraction with a water-immiscible solvent such as ethyl acetate, butyl acetate or chloroform. The substance MH435-A in the mycelium can be recovered by treating the mycelium with ethyl acetate, chloroform, methanol, ethanol, butanol, acetone or methyl ethyl ketone. It is also possible to subject the cultured broth as such without isolating the mycelium to the aforementioned extraction procedure. It is also possible to subject the mycelium to crushing followed by extraction. Counter-current distribution may be included in the extraction methods.

Another method of recovering the substance MH435-A from the cultured broth is based on adsorption. According to this method, the substance MH435-A-containing liquid material, such as cultured broth filtrate or an extract obtained by the aforementioned extraction procedure, is subjected to column chromatography, liquid chromatography or the like using an appropriate adsorbent such as activated carbon, alumina, silica gel or "DIAION HP20" (manufactured by Mitsubishi Chemical Industries, Ltd.). The objective substance MH435-A adsorbed onto the adsorbent is then eluted therefrom. The solution of the substance MH435-A thus obtained is concentrated to dryness under reduced pressure to obtain a crude product of the substance MH435-A as a white powder.

The crude MH435-A product thus obtained can be purified by carrying out the aforementioned extraction and adsorption procedures, if necessary, in combination, over a necessary number of times followed by recrystallization, if desired. For example, it is possible to accomplish purification by a combination of column chromatography using an absorbent such as silica gel, "SEPHADEX LH20" or "DIAION HP20" (manufactured by Mitsubishi Chemical Industries, Ltd.) or a gel filter; liquid chromatography using an appropriate solvent; counter-current distribution; and thin layer chromatography. Specifically, for instance, the crude powder of the substance MH435-A is dissolved in a small amount of chloroform and the solution is applied to a silica gel column which is developed with an appropriate solvent to elute the active components individually. The aimed active fractions are combined together and concentrated under reduced pressure. The concentrate is further subjected to thin layer chromatography, and the desired component is scraped off. Thus the objective substance can be isolated substantially as a single substance. In order to further purify the substance, it is also possible to apply high-performance liquid chromatography or crystallization from an appropriate solvent.

4. Chemical Modification of MH435-A/Production of MH435-B

The substance MH435-B of the present invention can be prepared by adding hydrogen to the substance MH435-A in the presence of a catalyst. The hydrogen addition reaction can be carried out by any methods suitable for the purpose, for example, by dissolving the substance MH435-A in methanol, adding platinum oxide to the solution and then reacting the mixture with hydrogen. The isolation and purification of the substance MH435-B thus obtained can be carried out, for example, by chromatography using silica gel or the like in accordance with the aforementioned procedures for the substance MH435-A.

In the above processes of incubation and purification, MH435 was traced by detecting the inhibition activity thereof by measuring the tyrosine specific protein kinase in test samples in accordance with the following method.

[Measurement of tyrosine specific protein kinase activity]

The measurement of tyrosin specific protein kinase activity was carried out by modifying the method of measuring enzyme activity described by G. Carpenter et al. in The Journal of Biological Chemistry, 254, 4874–4891 (1979) using the membrane fraction of human epithelial carcinoma cells A-431 with respect to the tyrosine specific protein kinase in the epidermal growth factor receptor. That is to say, the pre-incubation was carried out with 50 μl of 20 mM HEPES buffer (pH 7.4) containing 1 mM of $MnCl_2$, 100 ng of the epidermal growth factor, 40 μg of the A-431 membrane fraction, 7.5 μg of albumin, 3 μg of histone and the substance MH435-A or MH435-B at 0° C. for 10 min. Then, 10 μl of [Y-$^{32}$P]adenosine triphosphate (0.25 mCi/0.125 ml) was added to the mixture and the reaction was carried out at 0° C. for 30 min. A portion of the reaction product (50 μl) was taken out and adsorbed on Whatman filter paper No. 3 MM. The filter paper was dipped in ice-cooled TCA, left standing for 30 min. and taken out for washing with TCA, ethanol and ether. Then, $^{32}$P adsorbed on the filter paper was measured by counting the radioactivity (a). At the same time, count (b) was measured for the reaction product which was obtained by the same reaction and treated in the same manner as above except that the test sample was excluded, while counts (a') and (b') were measured for the reaction products in which the membrane fractions were further excluded, respectively. The inhibitory ratio with respect to the epidermal growth factor receptor kinase was then calculated from the equation $$[(a-a')/(b-b')] \times 100.$$

Physiological Activity of MH435

The substance MH435 according to this invention has antitumor activity and antimicrobial activity as shown below and is useful as a drug.

1. Inhibitory activity against tyrosine specific protein kinase

The 50% inhibitory concentrations of the substances MH435-A and MH435-B which were measured by the aforementioned method were respectively 0.55 μg/ml and 6.0 μg/ml.

2. Effects on cultured carcinoma cells

The substance MH435-A according to this invention inhibits at a very low concentration the proliferation of the cultured cells such as L1210 leukemia cells, IMC carcinoma cells, or Ki-NRK, ts Src-NRK and A-431 cells. (See Table 3 below.)

TABLE 3

| Cultured carcinoma cells | IC$_{50}$ ($\mu$g/ml) |
|---|---|
| L1210 | 2.41 |
| IMC carcinoma | 3.01 |
| Ki-NRK | 1.70 |
| ts Src-NRK (at 33° C.) carcinoma form | 2.00 |
| ts Src-NRK (at 39° C.) normal form | 3.60 |
| A-431 | 3.60 |

IC$_{50}$ was measured by inoculating the respective cells in dished (3–5×10$^4$ cells/dish), incubating the cells for 1 day (at 37° C.; CO$_2$ concentration, 5%), then adding the substance MH435-A, further incubating the resultant mixture for 3 days under the same conditions and finally counting the number of the cells.

3. Acute toxicity (LD$_{50}$)

The LD$_{50}$ value of the substance MH435-A according to this invention after a single intraperitoneal administration into a mouse was 200 mg/kg or more.

4. Antimicrobial activity

Minimum inhibitory concentrations (MIC) of the substance against various bacteria determined by the agar dilution method using Müller-Hinton culture medium are shown in the following Table 4.

TABLE 4

| | MIC ($\mu$g/ml) | |
|---|---|---|
| Bacteria tested | MH435-A | MH435-B |
| S. aureus 209 P | 50 | 50 |
| S. aureus Smith | 25 | 50 |
| S. aureus MS8710 | 50 | 50 |
| S. aureus MS9610 | 50 | 50 |
| M. lysodelkticus IFO 333 | 50 | 50 |
| B. Subtilis PCI 219 | 100 | 100 |
| B. cereus ATCC 10702 | 100 | 100 |
| Coryn. bovis 1810 | 100 | 100 |
| E. coli NIHJ | 100 | 100 |
| K. pneumoniae PCI 602 | 100 | 100 |
| Sal. typhi T-63 | 100 | 100 |
| Serr. marcessens | 100 | 100 |
| Prot. vulgaris OX19 | 100 | 50 |
| Pseu. aeruginosa A3 | 25 | 50 |

EXPERIMENTAL EXAMPLES

EXAMPLE 1

One platinum loopful of a slant culture of the strain MH435-hF3, an MH435-A-producing strain, was inoculated into the culture medium preliminarily sterilized at 120° C. for 20 min. and distributed in an amount of 110 ml in 500-ml Erlenmeyer flasks (the medium containing 3% of glycerol, 2% of fish meal and 0.2% of calcium carbonate, pH 7.4). The inoculated medium was subjected to aerobic shake culture at 180 rpm at 27° C. The production output of the substance MH435-A was checked periodically by measuring the anti-epidermal growth factor receptor kinase activity of the culture broth. As the result thereof, it was observed that the concentration of the MH435-A culture broth quantitatively measured in terms of the inhibitory activity against the epidermal growth factor receptor kinase reached a maximum after 4 days of incubation and kept stable during 2 days of further incubation, decreasing gradually thereafter.

EXAMPLE 2

A seed culture broth obtained by the incubation for 48 hours under the same cultural conditions as in Example 1 was inoculated in an amount of 3 ml into the same culture medium as in Example 1 and incubated for 96 hours as above. Five liters of the culture broth thus obtained was subjected to centrifugation to obtain 4.6 liters of a culture filtrate. 4.6 liters of the culture filtrate obtained was extracted with the equivalent volume of butyl acetate and concentrated to dryness under reduced pressure to obtain 360 mg of a crude powder. The crude powder thus obtained was adsorbed in a column packed with 20 g of silica gel "KIESEL GEL 60" (manufactured by Merck & Co., 70–230 mesh) and eluted stepwise with varying mixing ratios of chloroform-methanol. Fractions containing MH435-A were collected and concentrated to dryness under reduced pressure to obtain 110 mg of a crude powder. The epidermal growth factor receptor kinase inhibitory activity (IC$_{50}$) of the crude powder was 1.6 $\mu$g/ml.

The crude powder was dissolved in methanol, adsorbed in a reversed phase column for preparative high performance liquid chromatography packed with "NUCLEOSIL $_5$C$_{18}$" (manufactured by M. Nagel Co.) which had been equilibrated with a 20% aqueous methanol solution, and eluted with a 20% aqueous methanol solution at an elution speed of 8 ml/min. The eluate was fractionated into 10 ml aliquots. The active fractions were combined together and concentrated under reduced pressure, extracted with butyl acetate, concentrated again to dryness, dissolved in a small amount of ethyl acetate and crystallized from chloroform to obtain 60.3 mg of crystalline substance MH435-A. The epidermal growth factor receptor kinase inhibitory activity (IC$_{50}$) of the crystalline MH435-A was 0.55 $\mu$g/ml.

EXAMPLE 3

The crystalline substance MH435-A (23.4 mg) obtained in Example 2 was dissolved in 10 ml of methanol and one spatula of platinum oxide was added to the solution. The resulting solution was subjected to reduction treatment for 2 hours under hydrogen stream and then filtered. The filtrate was concentrated under reduced pressure, adsorbed on a thin layer of silica gel (KIESEL GEL 60F$_{254}$" manufactured by Merck & Co.), developed with a 1:1 solvent mixture of toluene and acetone. The separated MH435-B-containing portion was scraped off and eluted with ethyl acetate. The fraction thus obtained was concentrated and passed through a "SEPHADEX LH-20" column of 1.0×40 cm which had been equilibrated with methanol. The column was developed with the same solvent as was used in the thin layer chromatography. The eluate was concentrated to dryness under reduced pressure to obtain 10.1 mg of the substance MH435-B. The epidermal growth factor receptor kinase inhibitory activity (IC$_{50}$) of the substance MH435-B was 6.0 $\mu$g/ml.

What is claimed is:

1. A physiologically active substance, MH435, represented by the formula:

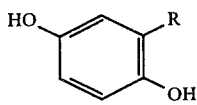 (I)
wherein R represents either of the following groups A and B
A: —CH=CH—NHCHO
B: —CH₂—CH₂—NHCHO.
2. The substance MH435 as claimed in claim 1 which is MH435-A where the substituent R in the formula (I) is —CH=CH—NHCHO.
3. The substance MH435 as claimed in claim 1 which is MH435-B where the substitutent R in the formula (I) is —CH₂—CH₂—NHCHO.
* * * * *